US010123839B2

(12) United States Patent
Netravali

(10) Patent No.: US 10,123,839 B2
(45) Date of Patent: Nov. 13, 2018

(54) SYSTEMS AND PROCESSES FOR PRE-OPERATIVE PLANNING AND PRECISE BONE REMOVAL FOR FEMOROACETABULAR IMPINGEMENT

(71) Applicant: CUREXO TECHNOLOGY CORPORATION, Fremont, CA (US)

(72) Inventor: Nathan A. Netravali, Palo Alto, CA (US)

(73) Assignee: THINK SURGICAL, INC., Fremont, CA (US)

(*) Notice: Subject to any disclaimer, the term of this patent is extended or adjusted under 35 U.S.C. 154(b) by 264 days.

(21) Appl. No.: 14/903,427

(22) PCT Filed: Jul. 11, 2014

(86) PCT No.: PCT/US2014/046399
§ 371 (c)(1),
(2) Date: Jan. 7, 2016

(87) PCT Pub. No.: WO2015/006721
PCT Pub. Date: Jan. 15, 2015

(65) Prior Publication Data
US 2016/0157936 A1    Jun. 9, 2016

Related U.S. Application Data

(60) Provisional application No. 61/845,307, filed on Jul. 11, 2013.

(51) Int. Cl.
*A61B 34/10* (2016.01)
*A61B 34/32* (2016.01)
(Continued)

(52) U.S. Cl.
CPC .............. *A61B 34/10* (2016.02); *A61B 17/16* (2013.01); *A61B 17/56* (2013.01); *A61B 34/32* (2016.02);
(Continued)

(58) Field of Classification Search
CPC ......... A61B 34/10; A61B 34/32; A61B 17/56; A61B 17/16
See application file for complete search history.

(56) References Cited

U.S. PATENT DOCUMENTS

| | | | |
|---|---|---|---|
| 5,824,085 A | 10/1998 | Sahay et al. | |
| 7,949,386 B2 | 5/2011 | Buly et al. | |

(Continued)

OTHER PUBLICATIONS

International Search Report dated Nov. 3, 2014 for International Application No. PCT/US2014/046399 filed Jul. 11, 2014.

*Primary Examiner* — Christopher Beccia
(74) *Attorney, Agent, or Firm* — Avery N. Goldstein; Blue Filament Law, PLLC

(57) ABSTRACT

Described herein are systems and processes for performing femoroacetabular impingement hip surgery using a robotic system. In general, the processes may include receiving an image of the at least one bone; creating three-dimensional models of the at least one bone; determining the location of the at least one bone such that a precise orientation is known; Using software to automatically generate a volume of the at least one bone to be removed; automatically performing robotically controlled milling to remove the impinging at least one bone; and providing a simulated kinematic analysis of motion of the at least one bone after it is removed. The process may further include the step of receiving input from the user, determined manually by said user, based on the three dimensional-models of the at least one bone, to modify a volume of the at least one bone to be removed.

20 Claims, 4 Drawing Sheets

(51) Int. Cl.
*A61B 17/16* (2006.01)
*A61B 17/56* (2006.01)
*A61B 90/00* (2016.01)

(52) U.S. Cl.
CPC . *A61B 2017/1602* (2013.01); *A61B 2017/564* (2013.01); *A61B 2034/104* (2016.02); *A61B 2034/105* (2016.02); *A61B 2090/3966* (2016.02); *A61B 2090/3975* (2016.02)

(56) References Cited

U.S. PATENT DOCUMENTS

| | | |
|---|---|---|
| 2007/0249967 A1* | 10/2007 | Buly .................... A61B 5/1121 600/595 |
| 2009/0157192 A1 | 6/2009 | Stuart |
| 2011/0082462 A1 | 4/2011 | Suarez et al. |
| 2011/0082468 A1 | 4/2011 | Hagag et al. |
| 2011/0152871 A1 | 6/2011 | Park et al. |
| 2012/0071893 A1* | 3/2012 | Smith ................ A61B 17/1664 606/130 |
| 2012/0209272 A1 | 8/2012 | Ranawat et al. |
| 2013/0006267 A1* | 1/2013 | Odermatt ............... B25J 9/1628 606/130 |
| 2013/0008550 A1 | 4/2013 | Meridew et al. |
| 2013/0009657 A1 | 4/2013 | Kang et al. |
| 2013/0085500 A1 | 4/2013 | Meridew et al. |
| 2013/0096574 A1 | 4/2013 | Kang |

\* cited by examiner

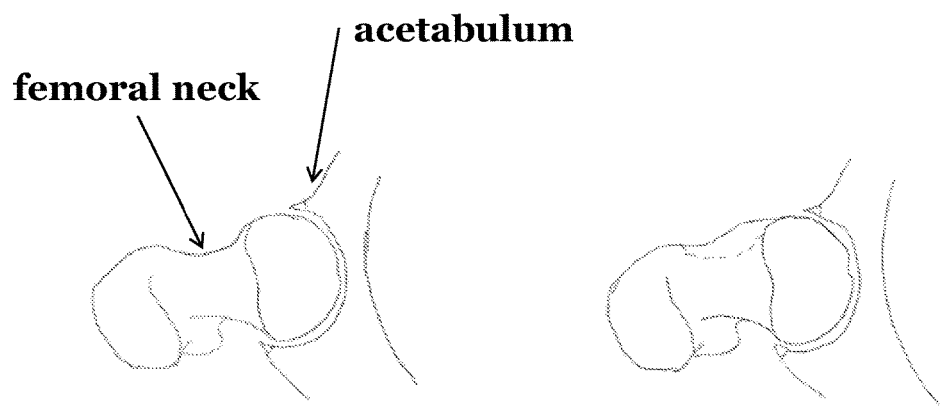
FIG. 1A
PRIOR
ART
FIG. 1B
PRIOR
ART
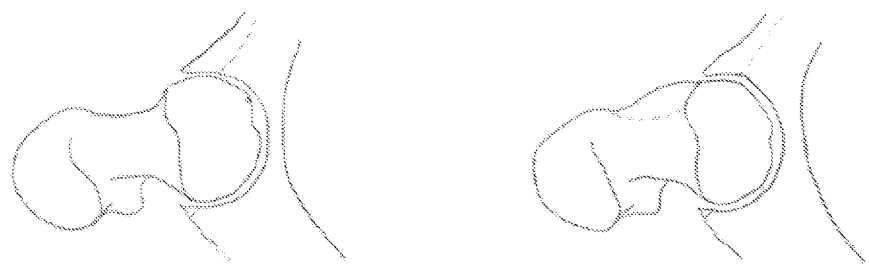
FIG. 1C
PRIOR
ART
FIG. 1D
PRIOR
ART

SYSTEMS AND PROCESSES FOR PRE-OPERATIVE PLANNING AND PRECISE BONE REMOVAL FOR FEMOROACETABULAR IMPINGEMENT

CROSS-REFERENCE TO RELATED APPLICATIONS

This application claims priority of U.S. Provisional Patent Application Ser. No. 61/845,307 filed Jul. 11, 2013 entitled "SYSTEMS AND PROCESSES FOR PRE-OPERATIVE PLANNING AND PRECISE BONE REMOVAL FOR FEMOROACETABULAR IMPINGEMENT", the entire contents of which is incorporated herein by reference in its entirety.

TECHNICAL FIELD

The present invention relates generally to computer-aided surgical systems, and more specifically to a new and useful system and process for planning and executing femoroacetabular impingement procedures.

BACKGROUND

Femoroacetabular impingement (FAI) has recently been suggested as a potential factor in the development of osteoarthritis of the hip. FAI can be defined as the abutment between the proximal femur and the acetabular rim and most typically affects young, active adults and presents clinically with groin pain. These structural abnormalities reduce the range of motion for these patients and repeated contact between the femoral neck and the acetabular cartilage and labrum can lead to degenerative changes in the hip joint cartilage. This cartilage can be either the articular cartilage covering the surface of the femoral head and the acetabulum or the labrum, which is a cartilaginous ring surrounding the rim of the acetabulum.

There are two distinct causes of FAI. The first type, known as "cam impingement", is due to a nonspherical portion of the femoral head abutting against the acetabular rim, especially during flexion and internal rotation. This can result in abrasion of the acetabular cartilage which may result in avulsion from the labrum and subchondral bone. Damage to the acetabular cartilage generally occurs in the anterosuperior area of the acetabulum and can lead to separation of cartilage from the labrum. The second type of FAI is known as 'pincer impingement' and is more common in middle-aged athletic women. It results from the contact of the femoral head-neck junction and the acetabular rim. Repeated abutment leads to degeneration of the labrum, resulting in ossification of the acetabular rim and deepening of the acetabulum. The subchondral damage is located fairly circumferentially and usually only includes a narrow strip of acetabular cartilage. Generally, cam and pincer impingements do not occur in isolation and most cases involve a combination of both mechanisms and are classified as a mixed cam-pincer impingement.

Due to the recently elucidated ties between FAI and the development of early osteoarthritis, treatment of FAI has become more commonplace. FAI is often treated with surgery as it will not heal on its own. The surgical technique most often employed is an open surgical technique. For cam-type morphologies, the aim is to recreate a normal concave contour of the femoral neck by removing bone through a series of sequential osteotomies of small sleeves of bone from the femoral head-neck junction. For pincer-type morphologies, either a resection osteoplasty of the acetabular rim is performed or a reorientation of a retroverted acetabulum by a periacetabular osteotomy.

Current techniques for femoroacetabular impingement require exposing the joint such that the user can view the bones. Additionally, during the procedure, the amount of bone resection necessary is left to the user's judgment, which may prove to be difficult to manage. Removal of too much bone may result in an increased risk of fracture in the femoral neck or pelvis, while removal of too little bone may not resolve the impingement issue. In one method of removal, the bone is removed using a tool, such as a burr, that is controlled by the surgeon without any guidance thereby resulting in bone removal that is variable.

Thus, there exists a need for a more accurate and precise method for determining the correct amount of bone to remove and then precisely removing that amount of bone.

SUMMARY OF THE INVENTION

Systems and processes are provided for a surgeon to use computer systems to accurately remove bone using robotic assistance, relieving impingement between the femur and the acetabulum. An embodiment of the inventive process for performing femoroacetabular impingement hip surgery by removing impinging bone from at least one bone using a robotic system includes the steps of receiving an image of the at least one bone of a patient, creating a three-dimensional model of the at least one bone of a patient, determining the location and amount of the at least one impinging bone to be removed, and automatically removing the at least one impinging bone using a robotically controlled milling apparatus to perform the hip surgery. The process also provides in some embodiments for registering the location of the at least one bone during the hip surgery such that a precise orientation and position of the at least one bone is known to the robotic system. The process also provides in some embodiments for automatically generating a volume of the at least one bone to be removed using software based on a simulated kinematic analysis. The process also provide in some embodiments for receiving input from a user, the input being determined manually by the user based on the three-dimensional models of the at least one bone, to modify said automatically generated volume of the at least one impinging bone to be removed.

A system for performing femoroacetabular impingement hip surgery by removing impinging bone from the at least one bone of a patient using a robotic system is also provided, the system including determining and making known to the robotic system the precise location, position and an orientation of the at least one bone during the hip surgery, using software based on a simulated kinetic analysis to automatically generate the volume of the at least one bone to be removed, receiving input from a user to manually modify the volume of the at least one bone to be removed, and providing a simulated kinematic analysis of motion of the at least one bone after it is removed.

BRIEF DESCRIPTION OF THE DRAWINGS

FIG. 1A is a prior art depiction that shows a normal hip morphology;

FIG. 1B is a prior art depiction that shows a cam impingement type morphology which results in reduced femoral head and neck offset;

FIG. 1C is a prior art depiction that shows a pincer impingement type morphology which results in excessive over coverage of the femoral head by the acetabulum;

FIG. 1D is a prior art depiction that shows a combined cam and pincer type morphology;

DETAILED DESCRIPTION OF THE PREFERRED EMBODIMENTS

The present invention has utility as a system and process for performing orthopedic surgery. The following description of various embodiments of the invention is not intended to limit the invention to these specific embodiments, but rather to enable any person skilled in the art to make and use this invention through exemplary aspects thereof. Disclosed herein are systems and processes to use computer systems to remove bone relieving impingement between the femur and the acetabulum. The removal of bone is performed using robotic assistance. Reference will be made herein to the treatment of hip joints and it should be understood that the present invention may be applied to removal of excess bone in other joints within the body and in any other bones found within the body. These other joints that are repaired through resort to the present invention illustratively include the hip joint, shoulder joint, ankle joint, wrist joint, finger joint, toe joint, or other joint. As used herein, a subject is defined as a human; or an animal of a non-human primate, a horse, a cow, a sheep, a goat, a dog, a cat, a rodent and a bird.

With reference to FIG. 1A, a prior art image of a normal hip joint is depicted with a normal femoral neck and acetabulum such that the femur is able to rotate without resulting in impingement. With reference to FIG. 1B, a prior art image of a cam impingement type morphology is displayed where there is a prominence on the femoral neck resulting in contact when the femur rotates. With reference to FIG. 1C, a prior art image of a pincer impingement type morphology is displayed where there is over-coverage by the acetabulum resulting in premature contact as the femur rotates. With reference to FIG. 1D, a prior art image of a mixed cam-pincer impingement type morphology is displayed in which both the femoral neck has a prominence and the acetabulum exhibits over-coverage resulting in multiple modes of impingement as the femur rotates.

Figure 2:
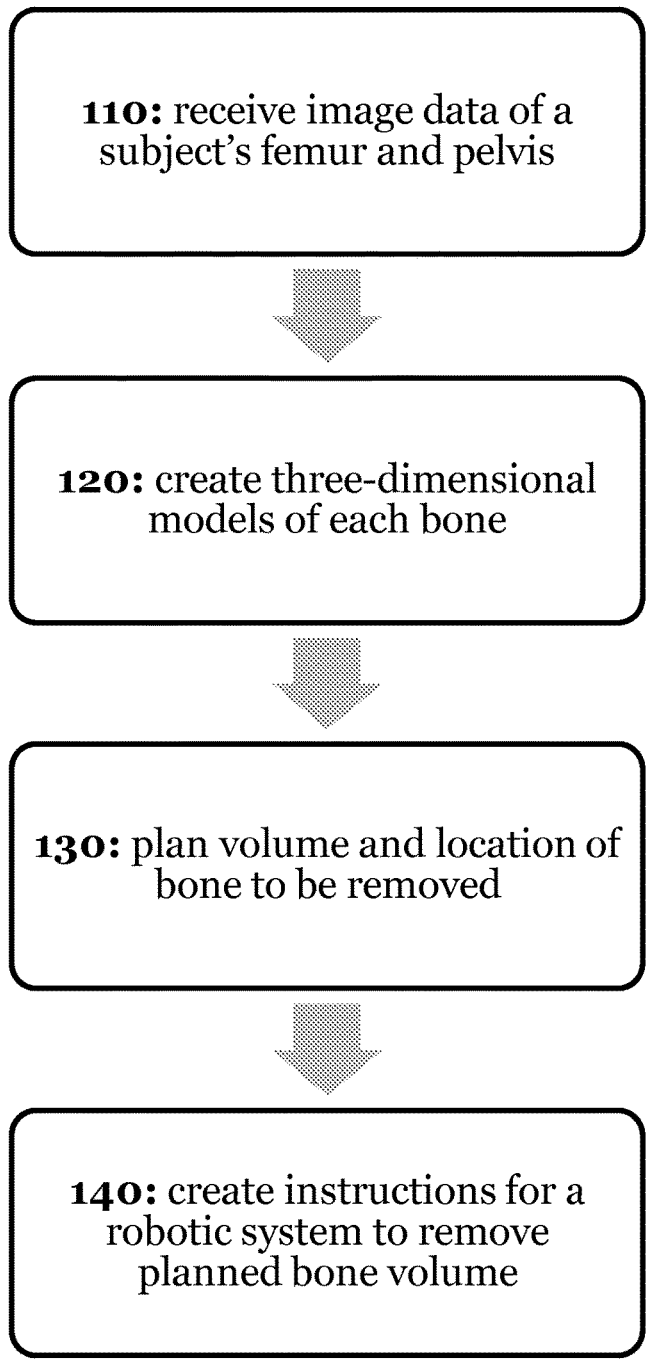
FIG. 2 is a flowchart depicting a specific embodiment of the present invention for using a computer system for preoperatively planning a femoroacetabular impingement surgery.

With reference to FIG. 2, an embodiment of an inventive process is detailed for receiving image data of a subject's bones including the femur and pelvis in block 110; creating three-dimensional (3D) models of the femur and pelvis in block 120; planning the volume and location of bone to be removed on the femur, pelvis, or both in block 130; and creating instructions for a robotic system to automatically remove the planned bone volume in block 140.

Figure 3A:
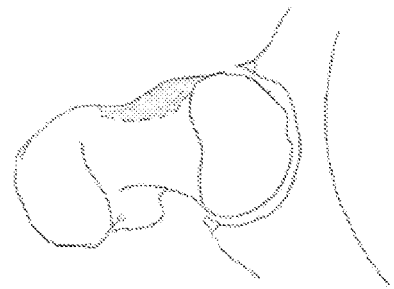
FIG. 3A shows the shaded bone to be removed in a cam impingement type morphology according to an embodiment of the present invention.
Figure 3B:
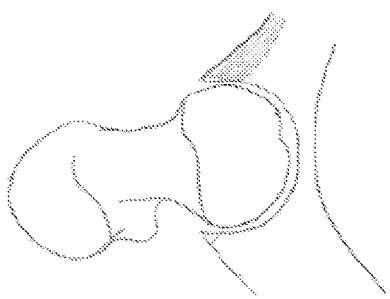
FIG. 3B shows the shaded bone to be removed in a pincer impingement type morphology according to an embodiment of the present invention.
Figure 3C:
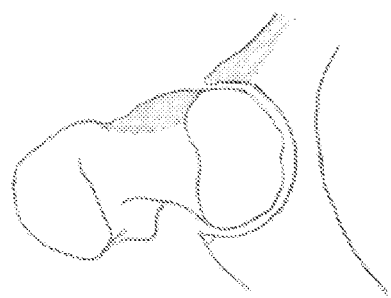
FIG. 3C shows the shaded bone to be removed in a combined type morphology according to an embodiment of the present invention.

With reference to FIG. 3A, the cam impingement type morphology is displayed with the prominence shaded or highlighted as it might be in preoperative planning software. With reference to FIG. 3B, the pincer impingement type morphology is displayed with the over-coverage of the acetabulum shaded or highlighted as it might be in preoperative planning software. With reference to FIG. 3C, the mixed cam-pincer impingement type morphology is displayed with the femoral neck prominence and over-coverage of the acetabulum shaded or highlighted as it might be in preoperative planning software.

Figure 4:
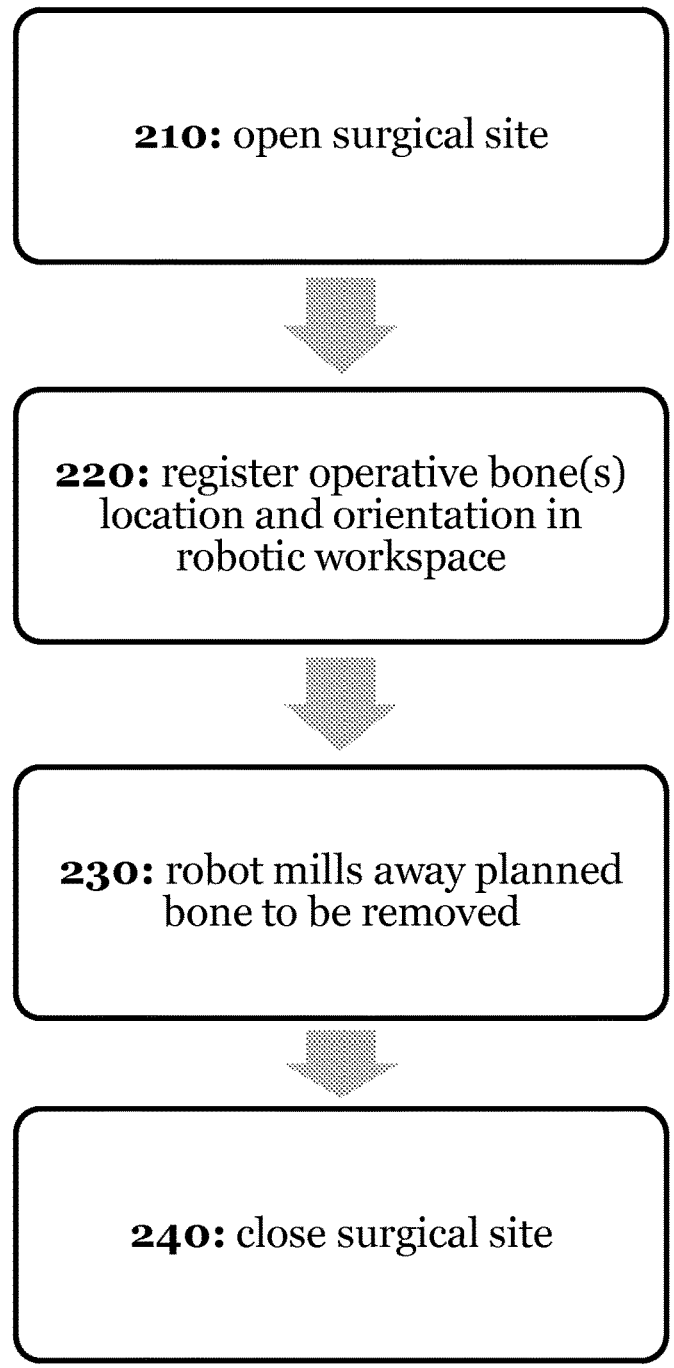
FIG. 4 is a flowchart depicting a specific embodiment of the present invention for using a computer-controlled robotic system to perform femoroacetabular impingement surgery according to a preoperative plan.

With reference to FIG. 4, an embodiment of an inventive process is detailed for opening the surgical site to provide access to the operative bone(s) which may be the pelvis and femur in block 210; registering the operative bone(s) within the workspace of the robot such that their orientations and locations are known in block 220; having the robot mill or cut the bone to be removed as planned in the preoperative planning software in block 230; and closing the surgical site in block 240.

With reference to FIG. 2, scan data of bone of a subject and prosthesis as illustrated in block 110 is readily provided from conventional sources such as CT, MRI, or X-ray scans of subjects' bones, or a combination thereof. The scan data may be collected by a system and process described herein or may alternatively, be collected prior to the FAI surgery.

With reference to FIG. 2, development of three-dimensional models of the bones as provided in block 120 may be performed readily using modeling software such as VSG Amira or Medviso Segment to convert imaging scans into models of the bone or may alternatively, be performed using other innovative technologies to convert imaging scans into models of the bone. In some embodiments only one bone may need to be modeled, while in others both the femur and acetabulum may need to be modeled.

With reference to FIG. 2, the preoperative planning as provided in block 130 involves determining the amount of overgrown or excess bone to be removed. In some embodiments, this may involve a simulated kinematic analysis in which the femur is rotated throughout a typical range of motion with respect to the pelvis to determine the locations of impingement. This simulated kinematic analysis may be done automatically by the preoperative planning software and may automatically select the bone that is being impinged or it may be performed manually by the user using his/her judgment. The user will have the option to view the location and amount of bone to be removed in two or three dimensions using the preoperative planning software. The bone to be removed may be shaded, highlighted, colored based on the depth to be removed, or otherwise demarcated as depicted in FIGS. 3A-3C. If the software automatically determines the amount of bone to be removed, the user will have the option to manually modify this region at his/her discretion. In some embodiments, the software may not provide assistance in determining the amount of bone to be removed and the user will manually select the bone to be removed. In still other embodiments, the software may provide the user with an initial estimate of the boundaries for the volumes of bone to be removed. In some embodiments, the software may provide a finite element or structural analysis to determine whether the remaining bone can withstand normal loading during activities of daily living. In some inventive embodiments, the software will provide a simulated virtual surgery in which the bone to be removed is removed and a kinematic analysis can be performed to ensure that there is free motion of the femur throughout a range of motion after the surgery. In some embodiments, the software will provide the ability to compare the bony geometry to that of the healthy contralateral bone in the same individual, or to the bony geometry of another healthy individual, or to the bony geometry of a group of healthy individuals.

Additionally, with reference to FIG. 2, block 140 in still other embodiments also functions to create instructions for a robotic system to automatically mill out the bone to be removed to accurately match the preoperative plan. One such robotic system is the ROBODOC System, manufactured by Curexo Technology Corporation of Fremont, Calif.

With reference to FIG. 4, the surgery to relieve the femoroacetabular impingement is provided at block 210 and begins by opening the surgical site. The method utilized to open the surgical site may be a traditional open approach, a minimally invasive incision approach, a laparoscopic approach or may alternatively, be an innovative approach to open the surgical site that is accepted in the field.

With reference to FIG. 4, the registration of the location of the bone intraoperatively within the workspace of the robot is provided at block 220. This serves to determine the precise location and orientation of the bone within the workspace of the robot. In some embodiments, this may be accomplished using fiducial markers placed into or on the bone. A fiducial marker is appreciated to be a material with an opacity that is different than that of surround subject tissue, an active device such as radio frequency identification (RFID) tag, or a combination thereof. In still other inventive embodiments, a registration guide is applied that fits on the bone, or a surface matching algorithm is used, or alternatively, any other method to determine the orientation of the subject's operative bone is used. In other embodiments, this may be accomplished using optical trackers, mechanical trackers, magnetic trackers, or ultrasound methods.

With reference to FIG. 4, the bone is removed using a robotic system as provided at block 230. The robotic system, in one embodiment, mills the planned volume of bone to be removed according to the preoperative plan. In other embodiments, the robotic system provides feedback or virtual constraints while the surgeon removes the bone using a milling bit to ensure that the surgeon is removing only the bone he had previously planned to remove. After the bone has been removed, the surgeon may close the surgical site using typical surgical methods as provided at block 240.

References recited herein are indicative of a level of skill in the art to which the invention pertains. These references are hereby incorporated by reference to the same extent as if each individual reference was explicitly and individually incorporated herein by reference.

As a person skilled in the art will recognize from the previous detailed description and from the figures and claims, modifications and changes can be made to the preferred embodiments of the invention without departing from the scope of this invention defined in the following claims.

What is claimed is:

1. A process for performing femoroacetabular impingement hip surgery by removing impinging bone from at least one bone using a robotic system comprising:
    receiving an image of the at least one bone;
    creating a three-dimensional models of the at least one bone;
    determining the location and amount of the impinging bone to be removed around the acetabulum or femoral neck; and
    automatically performing robotically controlled milling to remove the impinging bone to perform the hip surgery.

2. The process of claim 1 further comprising registering the location of the at least one bone during the hip surgery such that a precise position and an orientation of the at least one bone is known to the robotic system.

3. The process of claim 1, wherein a volume of the at least one bone to be removed is generated automatically by software based on a simulated kinematic analysis.

4. The process of claim 1, further comprising receiving input from a user to modify a volume of the at least one bone to be removed.

5. The process of claim 1 wherein volume of the at least one bone to be removed is determined manually by the user based on the three-dimensional models of the at least one bone.

6. The process of claim 1 further comprising providing a simulated kinematic analysis of motion of the at least one bone after it is removed.

7. A system for performing the process of claim 1.

8. A process for performing femoroacetabular impingement hip surgery by removing impinging bone from at least one bone using a robotic system comprising:
    receiving an image of the at least one bone;
    creating a three-dimensional models of the at least one bone;
    determining the location and amount of the impinging bone to be removed around the acetabulum or femoral neck;
    automatically performing robotically controlled milling to remove the impinging bone to perform the hip surgery; and
    registering the location of the at least one bone during the hip surgery such that a precise orientation and position of the at least one bone is known to the robotic system.

9. The process of claim 8, wherein a volume of the at least one bone to be removed is generated automatically by software based on a simulated kinematic analysis.

10. The process of claim 8, further comprising receiving input from a user to modify a volume of the at least one bone to be removed.

11. The process of claim 8, wherein volume of the at least one bone to be removed is determined manually by the user based on the three-dimensional models of the at least one bone.

12. The process of claim 8, further comprising providing a simulated kinematic analysis of motion of the at least one bone after it is removed.

13. A process for performing femoroacetabular impingement hip surgery by removing impinging bone from at least one bone using a robotic system comprising:
    receiving an image of the at least one bone;
    creating a three-dimensional models of the at least one bone;
    determining the location and amount of the impinging bone to be removed around the acetabulum or femoral neck;
    automatically performing robotically controlled milling to remove the impinging bone to perform the hip surgery; and
    automatically generating a volume of the at least one bone to be removed using software based on a simulated kinematic analysis.

14. The process of claim 13, further comprising receiving input from a user to modify a volume of the at least one bone to be removed.

15. The process of claim 13, wherein volume of the at least one bone to be removed is determined manually by the user based on the three-dimensional models of the at least one bone.

16. The method of claim 13, further comprising providing a simulated kinematic analysis of motion of the at least one bone after it is removed.

17. A process for performing femoroacetabular impingement hip surgery by removing impinging bone from at least one bone using a robotic system comprising:
   receiving an image of the at least one bone;
   creating a three-dimensional models of the at least one bone;
   determining the location and amount of the impinging bone to be removed around the acetabulum or femoral neck;
   automatically performing robotically controlled milling to remove the impinging bone to perform the hip surgery; and
   receiving input from a user, the input being determined manually by the user based on the three-dimensional models of the at least one bone, to modify said automatically generated volume of the at least one impinging bone to be removed.

18. The process of claim 17 further comprising registering the location of the at least one bone during the hip surgery such that a precise position and an orientation of the at least one bone is known to the robotic system.

19. The process of claim 17, wherein volume of the at least one bone to be removed is determined manually by the user based on the three-dimensional models of the at least one bone.

20. The method of claim 17, further comprising providing a simulated kinematic analysis of motion of the at least one bone after it is removed.

* * * * *